United States Patent [19]

Judd et al.

[11] Patent Number: 5,473,941
[45] Date of Patent: Dec. 12, 1995

[54] ENCAPSULATED ACCELEROMETER WITH FARADAY SHIELDING

[75] Inventors: John E. Judd; Yi H. Lo, both of Hamden, Conn.

[73] Assignee: Vibra-Metric, Inc., Hamden, Conn.

[21] Appl. No.: 100,704

[22] Filed: Jul. 30, 1993

[51] Int. Cl.⁶ .................................................. G01P 15/08
[52] U.S. Cl. ........................... 73/514.34; 73/658; 73/654
[58] Field of Search ......................... 73/517 R, 517 AV, 73/658, 654

[56] References Cited

U.S. PATENT DOCUMENTS

| | | | |
|---|---|---|---|
| 4,211,951 | 6/1980 | Jensen | 73/517 R |
| 4,858,470 | 8/1989 | Kincaid et al. | 73/654 |
| 4,884,250 | 11/1989 | Kitzinger et al. | 367/180 |
| 4,905,518 | 3/1990 | Kübler | 73/517 R |
| 5,130,600 | 7/1992 | Tomita et al. | 73/517 R |
| 5,218,870 | 6/1993 | Komurasaki et al. | 73/654 |

Primary Examiner—Richard Chilcot
Assistant Examiner—Max Noori
Attorney, Agent, or Firm—DeLio & Peterson

[57] ABSTRACT

An accelerometer with internal electronics is mounted within a Faraday shield and encapsulated within a non-electrically conductive material applied by hot injection molding at a high pressure to form a hermetically sealed case with integral strain-relief, cable bend protection, ground loop isolation and protection against EMI/RFI interference through both conduction and radiation. The accelerometer is shaped as a torus with the center hole providing center hole bolt mounting.

15 Claims, 2 Drawing Sheets

ENCAPSULATED ACCELEROMETER WITH FARADAY SHIELDING

BACKGROUND OF THE INVENTION

1. Field of the Invention

This invention relates to accelerometers of the type commonly used to monitor vibrations in industrial applications. More particularly, the invention relates to accelerometers intended for use in extremely rugged environments and exposed locations, where contact with hazardous industrial chemicals, mechanical shock and high levels of electromagnetic and radio frequency interference (EMI/RFI) are likely.

2. Description of Related Art

Accelerometers are widely used to monitor the vibration of electrical motors, pumps and the like in industrial applications, especially continuous production applications. Changes in the vibration levels, particularly in rotating machinery, provide an advance warning of problems such as excessive wear or an approaching bearing failure. With such warning, the problems can be dealt with during regularly scheduled maintenance periods and expensive unplanned shutdowns can be avoided.

In industrial applications of this type, accelerometers are exposed to numerous hazards. Accelerometers near pumps are often splashed by acids, coolants, caustic solvents, oils, hydraulic fluids or other industrial chemicals that over time migrate into a conventional accelerometer and cause it to fail.

Accelerometers monitoring electrical motors, or which are near industrial electrical equipment, are exposed to high levels of EMI/RFI noise that can seriously interfere with operation of the electrical components in the accelerometer. Interference may be radiated directly into the accelerometer or conducted in through the case and mounting bolts.

Ground loops are also a particular problem where grounded case accelerometers have been used. Attempts to alleviate such problems by isolation stud mounting (which electrically insulates the case of the accelerometer from the equipment being monitored) are often defeated in harsh environments as the exterior of the accelerometer and the isolation stud are contaminated over time by conductive industrial materials.

Finally, manufacturing facilities are a notoriously rough location for sensitive monitoring equipment. Accelerometers mounted on industrial machinery may be exposed to high G-force impacts and other physical abuse. The cables connected to the accelerometers may be inadvertently pulled excessively, or bent to very sharp angles, leading to premature failure.

Prior art accelerometers have proven to be deficient in the rugged environments described above. None have provided the necessary resistance to industrial chemicals and impact, EMI/RFI noise rejection and ground isolation in combination with high quality electronics, sensitivity, and ease of installation needed in the industrial environment.

Bearing in mind the problems and deficiencies of the prior art, it is therefore an object of the present invention to provide a hermetically sealed accelerometer which has excellent resistance to most industrial chemicals in combination with ground isolation, EMI/RFI resistance and an integral cable with superior cable bend and strain relief protection.

A further object of the invention is to provide an accelerometer with the properties identified above that includes internal circuitry with a low impedance output.

Yet another object of the invention is to provide an accelerometer which is easy to mount. Still other objects and advantages of the invention will in part be obvious and will in part be apparent from the specification.

SUMMARY OF THE INVENTION

The above and other objects, which will be apparent to those skilled in the art, are achieved in the present invention which is directed to an accelerometer including a sensor sensitive to accelerations, an electrical circuit, preferably including impedance transforming means and amplifier means with a low impedance output, and a cable connected to the output of the electrical circuit.

The sensor and electrical circuit are mounted within a housing adapted for mounting to a mounting surface. The housing comprises a shield and an encapsulant completely surrounding the shield. The shield is formed of an electrically conductive material extending substantially completely around the sensor and the circuit, forming a Faraday shield which prevents electromagnetic interference from entering the accelerometer. The encapsulant is formed of an electrically nonconductive material which is highly resistant to impact and all types of industrial chemicals. The encapsulant extends substantially completely around the shield and physically protects, hermetically seals and electrically isolates it from the environment.

The encapsulating material is applied by hot injection molding under very high pressure. Strain relief is provided by mechanically connecting a cable sleeve to the cable and making all electrical connections prior to applying the encapsulating material. The high pressure, which forces encapsulating material into all openings, drives the encapsulating material into direct sealing contact with the insulation on the cable. This forms the hermetic seal which is highly resistant to moisture and the migration of all types of industrial contaminants.

The sensor is preferably a piezoelectric sensor operating in shear mode. The shield forming the housing is approximately shaped as a torus. The central opening of the torus receives a single bolt, providing a simple, but effective single point mount to the mounting surface. The encapsulant isolates the bolt from the shield providing complete ground isolation.

BRIEF DESCRIPTION OF THE DRAWINGS

For a fuller understanding of the invention, reference should be made to the following description taken in connection with the accompanying drawings, in which.

DESCRIPTION OF THE PREFERRED EMBODIMENT(S)

Figure 1:
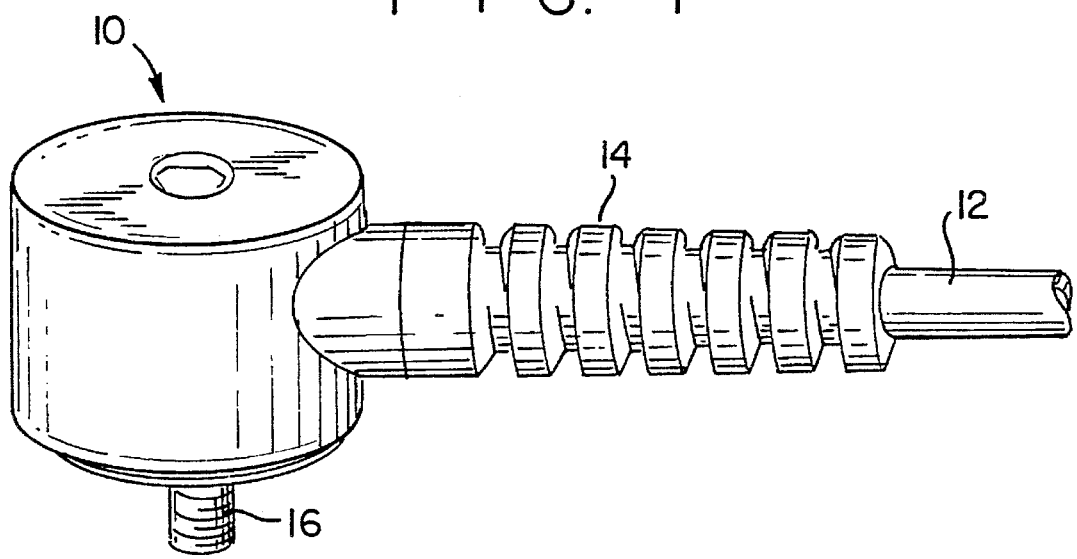
FIG. 1 is a perspective view of an accelerometer according to the present invention.

Referring to FIG. 1, the accelerometer generally includes an accelerometer contained within a housing 10. The housing is approximately doughnut-shaped, i.e. toroidally shaped, with a mounting bolt 16 passing through the center opening. A connection cable 12 makes connection at one end to the accelerometer through a cable boot 14 which provides cable bend protection. A connector of any desired type (not shown) is connected to the other end of the cable 12.

Figure 2:
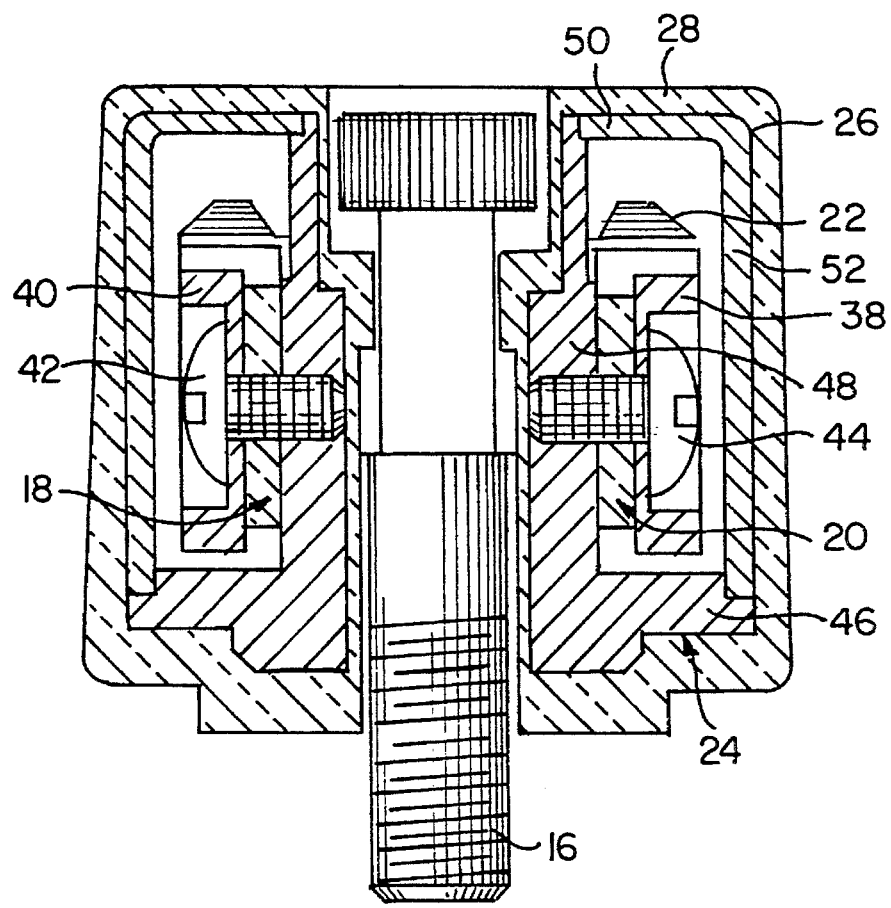
FIG. 2 is a cross sectional view of the accelerometer taken in a plane perpendicular to the axis of the cable and through the axis of the mounting bolt.
Figure 3:
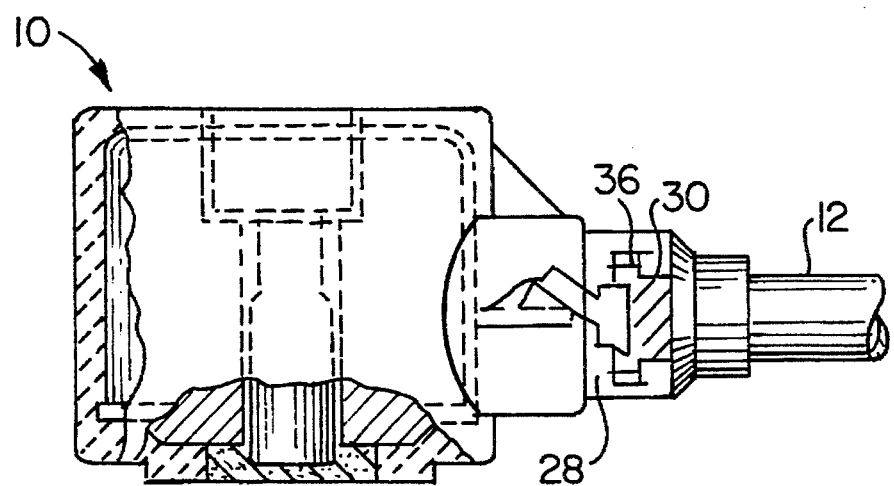
FIG. 3 is a partial cross sectional view from the side taken through the axis of the mounting bolt and through the axis of the cable.
Figure 4:
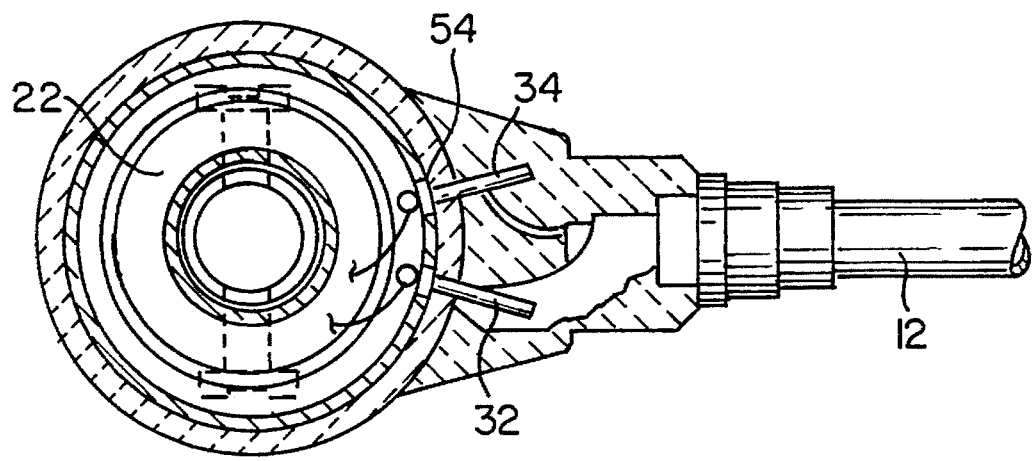
FIG. 4 is a partial cross sectional view of the accelerometer taken perpendicular to the mounting bolt.

Referring to the cross sectional views of FIGS. 2 through 4, it can be seen that the principal working components of the accelerometer include a piezoelectric sensor composed of two elements 18, 20 mounted on either side of the center opening and an electrical circuit 22 mounted on a ring shaped circuit board (see FIG. 4) that surrounds the center opening.

In the preferred design, the circuit 22 includes impedance transforming means and an amplifier so that the circuit output has a low impedance. In the most highly preferred design, the circuit is provided with reverse voltage protection, temperature equalization and electrostatic discharge protection with known techniques. The circuit is also provided with a factory preset sensitivity for the accelerometer at 100 mv/g (millivolts per g force) within an accuracy of ±5%. This makes the sensors interchangeable in most applications without requiring recalibration by the user.

The circuit 22 and piezoelectric elements 18, 20 are mounted within a Faraday shield composed of two elements 24, 26 acting as a base and a cap. The first element 24 has an annular base plate portion 46 and an inner cylindrical portion 48. The bottom of the inner cylindrical portion is connected to the base plate portion. The second element has an annular top plate portion 50 and an outer cylindrical portion 52. The inner and outer cylindrical portions 48, 52 are coaxially located when the two shield elements 24, 26 are assembled. The annular portions 46, 50 enclose the space between the cylindrical portions forming a squared-off torus (with vertical walls and a horizontal top and bottom) that completely surrounds and encases the circuit and piezoelectric elements.

The only opening in the shield is a small insulated opening 54 through which the vibration signal is passed on conductor 34 to the cable 12. The result of completely surrounding the circuit with a conductor is to form a Faraday shield that excludes EMI/RFI interference from the interior which might prevent proper operation.

The Faraday shield 24, 26 is in turn completely encapsulated within an electrically nonconductive encapsulating material 28. The encapsulating material electrically isolates the shield from the environment, including the mounting surface and the mounting bolt 16, to provide ground isolation and protect against the formation of ground loops.

As can be seen in the enlarged scale drawing of FIG. 2, the encapsulating material extends into the central opening of the shield to electrically isolate the mounting bolt 16 from the Faraday shield. The encapsulating material also traps the mounting bolt so that it will not become separated during shipping or handling, while still permitting it to rotate as necessary when the bolt is being fastened to the mounting surface.

FIG. 3 shows the accelerometer without the cable boot 14 around the cable 12. Cable 12 is preferably a coaxial cable and the outer conductor (shield conductor) of the coaxial cable is connected to the Faraday shield at 32. The center conductor of the coaxial cable 12 is connected to the circuit through an insulated pass through connector 34.

A cable sleeve 30 is crimped onto the cable 12 to make a firm connection thereto prior to the encapsulating process. The sleeve 30 has mechanical connection means in the form of protrusions 36 which are engaged by the encapsulant 28 during the encapsulating process. This solidly locks the cable to the accelerometer to provide superior strain relief. The boot 14 is pre-manufactured and slipped over the cable 12 and adhesively attached to provide cable bend protection at the joint between the cable 12 and the accelerometer 10.

As can be seen in FIGS. 2 and 3, the encapsulating material 28 not only extends around the visible exterior of the device but also extends below the base portion 46 of the Faraday shield 24. This electrically isolates the accelerometer from the mounting surface to prevent ground loops and conducted EMI/RFI interference. The combination of the internal Faraday shield and case ground isolation provides excellent noise rejection for both radiated and conducted EMI/RFI noise.

In addition to providing strain relief and electrical isolation, the encapsulating material provides hermetic sealing and impact resistance. The hermetic sealing occurs as a result of the encapsulating process which applies the encapsulating material in a hot injection molding process, preferably at a pressure of 1,000 pounds per square inch ($6.8 \times 10^6$ Pascals) or more.

The encapsulating material should have high impact strength, low flammability, high corrosion resistance, high flexural and tensile strength, high compressive strength, low moisture absorption, low heat distortion, high hardness, a broad operating temperature range from −65° F. to +400° F. (−54° to 204° C.) in addition to high electrical resistivity and excellent resistance to a broad range of chemical compounds including acids, alkaline coolants and caustic solvents, gear, brake and engine oils, hydraulic fluids and fuels as well as bleaches and chlorine. Appropriate materials include thermosetting plastics, vinylesters including glass fiber reinforced vinylesters, glass fiber reinforced polyesters and mineral filled epoxies. The preferred material, selected after considerable evaluation of alternatives, is a vinylester based product such as vinylester c108 manufactured by Industrial Dielectrics, Inc. of Noblesville, Ind.

The cable also requires certain properties to perform well in the harsh environments to which the accelerometers of the invention are exposed. These properties include good resistance to all the industrial chemicals referred to above, good high temperature characteristics in the temperature range to be expected during the injection molding process, high pull strength, good flexibility and excellent electrical shielding. High quality coaxial electrical cables employing insulation of fluorocarbon elastomers, tetrafluorethylene-propylene polymers and silicon are all suitable, with tetrafluorethylene-propylene polymers being slightly preferred.

The piezoelectric elements 18, 20 are mounted in shear mode by mounting the elements 18, 20 on opposite sides of the inner cylindrical portion 48 between the inner cylindrical portion and masses 38, 40. Screws 42, 44 pass through the masses and into the inner cylindrical portion 48. Whenever the accelerometer is subjected to a vertical acceleration, the masses 38, 40 apply a shear force to the piezoelectric crystal which is amplified by the circuit 22 and transmitted out cable 12. The shear mode design minimizes base strain and thermal transient errors.

Other types of sensing may also be employed in other applications such as compression mode or a piezo resistive bridge mode sensing design. Variations in the design, within the skill of the art, may be made to provide velocity dependent output or multiaxial sensing.

The Faraday shield is preferably made of stainless steel, but may also be made of other electrically conductive materials.

It will thus be seen that the objects set forth above, among those made apparent from the preceding description, are efficiently attained and, since certain changes may be made in the above construction(s) without departing from the spirit and scope of the invention, it is intended that all matter contained in the above description or shown in the accompanying drawing(s) shall be interpreted as illustrative and not in a limiting sense.

Thus, having described the invention, what is claimed is:

1. An accelerometer comprising:
   a sensor sensitive to accelerations;
   an electrical circuit having an input connected to the sensor and a low impedance output;
   a cable connected to the output of the electrical circuit;
   a toroidally shaped housing adapted for mounting to a mounting surface by means of a bolt passing through the toroidally shaped housing comprising:
   a shield formed of an electrically conductive material, the shield extending substantially completely around the sensor and the circuit to prevent electromagnetic and radio frequency interference; and
   an encapsulant formed of an electrically nonconductive material, the encapsulant forming the exterior of the housing and extending substantially completely around the shield, the encapsulant hermetically sealing the housing to the cable to provide strain relief between the cable and the housing at a point exterior of the shield and electrically isolating the shield and the accelerometer from the mounting surface.

2. An accelerometer according to claim 1 further including a cable sleeve attached to the cable, the cable sleeve including mechanical connection means engaged by and encapsulated within the encapsulant to provide strain relief.

3. An accelerometer according to claim 1 wherein the cable contains a cable shield surrounding at least one inner wire in the cable, the inner wire being connected to the output of the circuit and the cable shield being connected to the shield surrounding the sensor and circuit.

4. An accelerometer according to claim 3 wherein the cable is a coaxial cable.

5. An accelerometer according to claim 1 wherein the sensor is a piezoelectric sensor.

6. An accelerometer according to claim 5 wherein the sensor is mounted for shear mode sensing of accelerations.

7. An accelerometer according to claim 6 wherein the housing is shaped as a torus with a central opening and the piezoelectric sensor is composed of two elements mounted for shear mode sensing on opposite internal sides of the central opening.

8. An accelerometer according to claim 1 wherein the shield comprises:
   a first element having an annular base plate portion and an inner cylindrical portion with a top and a bottom, the bottom of the inner cylindrical portion being connected to the base plate portion of the first element, and
   a second element having an annular top plate portion and an outer cylindrical portion with a top and a bottom, the top of the outer cylindrical portion being connected to the top plate portion;
   the first and second elements engaging one another to form the shield.

9. An accelerometer according to claim 8 wherein the sensor includes two piezoelectric sensor elements mounted on opposite sides of the inner cylindrical portion for shear mode vibration sensing.

10. An accelerometer according to claim 9 wherein the electrical circuit is mounted on a ring-shaped circuit board positioned around the inner cylindrical portion.

11. An accelerometer comprising:
    a piezoelectric sensor;
    an electrical circuit including an amplifier with an input connected to the sensor and a low impedance output;
    a Faraday shield extending substantially completely around the piezoelectric sensor and the electrical circuit; and
    a cable including at least one wire and an insulating coating surrounding the wire, the wire extending through the Faraday shield and being connected to the output of the electrical circuit;
    the Faraday shield being substantially completely encapsulated within an electrically nonconductive material applied by hot injection molding at a pressure of at least 1000 pounds per square inch, the encapsulating material contacting the insulating coating surrounding the wire and forming a hermetic seal therewith around the Faraday shield.

12. An accelerometer according to claim 11 further including a cable sleeve attached to the cable, the cable sleeve including mechanical connection means engaged by and encapsulated within the electrically nonconductive material.

13. An accelerometer comprising:
    a two element piezoelectric sensor mounted for shear mode sensing;
    an electrical circuit including an amplifier connected to the two elements of the piezoelectric sensor and having a low impedance output, the electrical circuit being reverse voltage protected and temperature equalized;
    a Faraday shield with an insulated opening forming a wire entrance through the shield, the Faraday shield extending substantially completely around the piezoelectric sensor and the electrical circuit and shaped as a torus having a central opening;
    a coaxial cable including:
      a center conductor extending through the insulated opening in the Faraday shield, connected to the output of the electrical circuit,
      a shield conductor connected to the Faraday shield;
      an insulating coating surrounding the coaxial cable, and
      a connector at a terminal end of the coaxial cable;
    a cable sleeve connected to the coaxial cable including protruding elements forming a mechanical connection means; and
    an encapsulant substantially completely encapsulating the Faraday shield within an electrically nonconductive, impact resistant, industrial chemical resistant encapsulating material, the encapsulating material being applied by hot injection molding to hermetically seal the Faraday shield, the insulated opening and the coaxial cable;
    the encapsulating material engaging the protruding elements of the cable sleeve to provide strain relief for the coaxial cable.

14. An accelerometer according to claim 13 wherein the encapsulating material is selected from the groups consisting of thermosetting plastics, vinylesters including glass fiber reinforced vinylesters, glass fiber reinforced polyesters and mineral filled epoxies.

15. An accelerometer according to claim 14 wherein the encapsulating material comprises a vinylester.

* * * * *